US00PP09205P

United States Patent [19]

Klemm

[11] Patent Number: Plant 9,205

[45] Date of Patent: Jul. 18, 1995

[54] GERANIUM PLANT 'KLEMIGA'

[76] Inventor: Siegfried Klemm, Hanfäcker 8, D 70378 Stuttgart, Germany

[21] Appl. No.: 285,865

[22] Filed: Aug. 4, 1994

[51] Int. Cl.[6] ..... A01H 5/00
[52] U.S. Cl. ..... Plt./87.12
[58] Field of Search ..... Plt. 87.12

*Primary Examiner*—James R. Feyrer
*Attorney, Agent, or Firm*—Arnold, White & Durkee

[57] ABSTRACT

Geranium Klemiga is a new and distinct cultivar of germanium, botanically known as *Pelargonium*×*zonale* Hybriden. It is distinguished from other geranium plants by its neon pink flower, color, medium green foliage, and robust hairy appearance.

1 Drawing Sheet

BACKGROUND OF THE NEW PLANT

Klemiga is a product of a breeding program that had the objective of developing well-shaped, orderly filled, double or semi-double orange flowers with dark foliage. Klemiga originated from an unidentified pollen parent and an unidentified seed parent. Seed was not collected as random. Crosses were made between groups of parent plants with dark pink or neon pink flowers and others with dark leaves. Seeds were collected from these crosses without identifying the parent plant. One of these seeds produced a new cultivar with dark pink flowers, medium green foliage and a robust and hairy appearance. Unexpectedly, the new cultivar had dark pink flowers, medium green foliage, and a robust and hairy appearance. Neither parent has been released to the public nor been commercialized.

The new cultivar was discovered in 1991 in Stuttgart, Germany and selected by the inventor as one flowering plant from among the progeny of an unidentified seed parent and an unidentified pollen parent in a controlled environment. The new seedling was obtained after cultivation of the seed parent with the pollen parent. Klemiga differed from either parent in having a dark pink color in contrast to the orange or salmon color of the parent plants.

Compared with its parents, Klemigas has pink flowers and medium green foliage in contrast to the orange and dark-leaved foliage of the parents. Klemiga requires 23 days to root after cuttings. Precocity is judged to be early to medium.

The first act of asexual reproduction of Klemiga was accomplished when vegetative cuttings were taken from the initial selection in a controlled environment in greenhouses in Stuttgart, Germany by the inventor or technicians working under the supervision of the inventor. Horticultural examination of selected plants demonstrated that the combination of characteristics herein disclosed for Klemiga are firmly fixed and are retained through successive generations of asexual reproduction.

Klemiga has not been observed under all possible environmental conditions. The phenotype may vary significantly with variations in environment such as temperature, light intensity, and daylength. The following observations, measurements, and comparisions described plants grown in Stuttgart, Germany under conditions that approximate those used in commercial pratice. Similar characteristics are found when the plant is grown under controlled environmental conditions in Italy, Germany Teneriffe, and the Netherlands.

Compared to other geranium varieties, Klemiga appears to be unique because of flower color, a flower shape similar to the camellia and the overall combination of flower shape and hairy, grayish-green appearance of the foliage.

Klemiga most closely resembles Klefa. Klefa is too early and too floriferous to have high market value because of its short branches and failure to produce enough leaves to provide a desirable appearance. Klefa is more floriferous than Klemiga, but the regular compact growth of Klemiga and the filling of the flower combines to give it a very desirable appearance. The weather resistance of Klemiga's flowers and foliage is excellent. The new cultivar also maintains continuity in flowering and is suitable for growth in most climates. It is more floriferous in hot climates, but plants tend to be shorter when the climate is consistently too hot. The flower color of Klemiga is new, bright, and highly attractive. Flower filling and flower form are particularly unique features. While the umbel size and shape may not be unusual, the coarse tomentum of the foliage and the brightly multicolored flower parts of this plant offer a starkly attractive and interesting contrast which is believed to have not been previously reported in the species.

DESCRIPTION OF THE PHOTOGRAPH

The accompanying color photograph of Klemiga illustrates typical inflorescence and leaf characteristics of the new plant. The plant was photographed using professional photographic techniques. The view is taken against a medium blue background that illustrates flower color closest to the color values in accordance with The Royal Horticultural Society Colour Chart. The background highlights the dark pink flower color.

DESCRIPTION OF THE PLANT

The following description uses color references from The Royal Horticultural Society Colour Chart. The color values were determined under prevailing conditions of natural daylight in a greenhouse environment duting the month of March in Stuttgart, Germany.

The following traits have been repeatedly observed and are determined to be basic characteristics of Klemiga that in combination distinguish the geranium as a new and distinct cultivar. These characteristics include a dark pink flower color with a large camellia-like floret petal shape.

Classification:

*Botanical.*—*Pelargonium* × *zonal Hybriden.*

*Commercial.*—Klemiga, Zonale Geranium.

The plant:

*Form.*—Bush.

*Shape.*—Round, symmetrical.

*Height.*—Normally maintains a height of 180 mm during the summer season, but may attain height near 200 mm by the end of the season.

*Growth.*—Upright, compact, slow to medium growth rate.

*Time from rooted cutting to flowering.*—95 days (under commerical greenhouse conditions).

*Pinching to induce branching.*—Not required; plant readily branches from nasal nodes.

*Stem length.*—110 mm to 120 mm (indoors); 100 mm (outdoors).

*Internode length.*—10 mm.

*Leaf stem length.*—40–60 mm (greenhouse conditions).

*Branching character.*—Very good.

*Number of stems per stalk.*—2.

*Number of stalks per plant.*—4.

*Foliage.*—Quantity — medium, robust. Shape — kidney shaped or half round (sinus normally open). Margin type — weakly bicrenated. Leaf size — average leaf length 4.5 cm, average leaf width 7–8 cm. Texture — smooth (leaf surface is hairy). Color: Upper side — 146A to 148A (difficult to determine because of hairy surface). Under side — 146B. Zonation — none.

Inflorescence:

*Blooming habit.*—Continuous (pinching not necessary to remove spent umbels), profuse (Spring to end of September).

*Cluster size.*—(Measured when more than 12 florets are open).

*Diameter.*—95 mm.

*Depth.*—70 mm.

*Cluster shape.*—Not round because of only a few florets.

*Umbel shape.*—Elliptic.

*Petalage.*—8–10.

Florets: Number of Florets/Umbel — 20. Size — 60 mm. Fullness — Double. Shape — Cup shaped becoming flat with maturity. Camellia-like with very broad petals. Perfect — Contains both pistils and stamens but not all stamens have anthers and bring pollen; some anthers are deformed and degenerated.

*Arrangement.*—Imbricated.

*Margin type.*—Entire.

*Petal persistence.*—6 days without pollination.

*Texture.*—Soft.

*Appearance.*—Satiny with some petals showing a pattern of short white streaks on the upper surface just above the claw.

*Color.*—Outer Petal/Floret — body — 52A. Base and border — 55A. Reverse Side — 50B. Inside Petal/Floret — Body — 57A to 57C (exact match with RHS color chart difficult for neon pink color). Base — 57C. Reverse Side.—50B.

*Petal size.*—Up to approximately 3 cm in length and up to approximately 2.5 cm in width.

*Shape.*—Of inconsistent size and shape, frequently folded or flexed.

*Petaloids.*—Number — 3–7. Color — 58B. Size — 5–23 mm in length and 2–7 mm in width.

*Flower stem (petiole).*—Length — 28 mm. Strength — Strong. Color — Green and brown (at the sepals).

*Petiole arrangement.*—Typical of species; petioles radiate outwardly from apex of peduncle.

*Discoloration after full bloom.*—Not noticeable, occasionally a little lighter in color.

*Effect of heat or rain.*—Negligible (very good "self cleaning").

*Persistence.*—Mature flowers dry and petals fall. If no fertilization has taken place, the entire peduncle dries and abscises.

*Disease resistance.*—Botrytis (flowers and foliage).

*Foliage.*—None.

*Lasting quality.*—Plant — 14–16 days. Cut flower — 4–5 days.

The lasting quality is determined by observing how long flowering clusters maintain their appearance without picking off the old florets. Additionally, observations are made on how many days it requires from the day when the first floret opens to the day when the last floret opens. This time period depends on the number of florets found in a single cluster and this number with geraniums generally varies from 20 to more than 70. The description indicates the amount of time the flowers maintain their appearance.

Bud:

*Average diameter.*—10 mm.

*Average depth.*—19 mm.

*Shape.*—Rosebud-like appearance, ovoid.

*Rate of opening.*—Somewhat quicker than average for other comparable geranium plants.

*Color of petals.13* When sepals first divide — light pink. When petals begin to unfurl — dark pink.

Sepals:

*Shape.*—Long and pointed.

*Number.*—5.

*When flowers open.*—Sepals stand up.

*Color.*—Inside — 146C. Outside — 146B.

*Buds and flowering clusters appearing at the same time.*—Young plants (April) — 1 large bud, 2 flowering clusters. Mature plant (May) — 4 mature clusters (from day when plant is marketable to middle of May when plant is placed outdoors).

*Clusters appearing during outside culture.*—90 or more if the summer is hot (May to September).

Reproductive organs:

*Stamens.*—4–5 (not all are fertile) arranged around the ovaries.

*Anthers.*—2 mm.

*Filaments.*—7 mm.

*Pistils.*—Normal, with articulated, six-lobed stigma.

*Styles.*—Length — 8–9 mm. Color — green (ovaries) and dark pink (part between stigmas and ovaries).

*Stigmas.*—Dark pink.

*Fertile.*—Yes.

*Length of seed.*—3–4.5 mm.

*Color of seed.*—Brown.

*Amount of pollen.*—Copious.

*Color of pollen.*—Dark orange.

What is claimed is:

1. A new and distinct geranium cultivar substantially as herein described and shown, characterized by its dark pink flowers and hairy gray-green foliage.

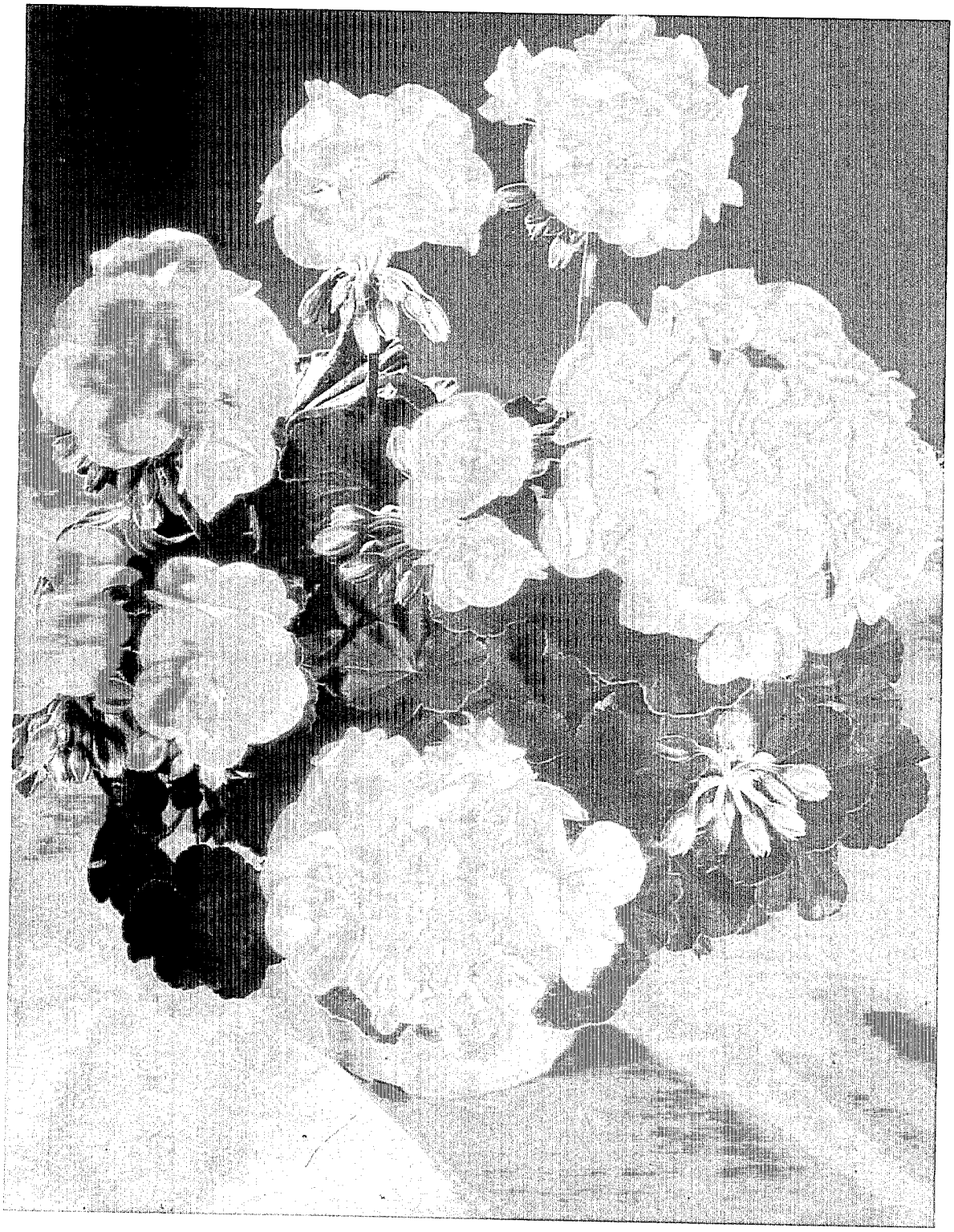

* * * * *